United States Patent [19]

Kordis

[11] 4,254,766
[45] Mar. 10, 1981

[54] SPLINTING DEVICE

[76] Inventor: Joel H. Kordis, 240 Emerald Dr., Vista, Calif. 92083

[21] Appl. No.: 56,818

[22] Filed: Jul. 12, 1979

[51] Int. Cl.[3] .............................................. A61F 5/04
[52] U.S. Cl. .................... 128/87 R; 128/133
[58] Field of Search ...................... 128/87 R, 85, 87 A, 128/89 R, 90, 77, 133, 134; 2/16, 18; 273/54 B

[56] References Cited

U.S. PATENT DOCUMENTS

| 3,196,870 | 7/1965 | Sprecher et al. | 128/87 R X |
| 3,408,077 | 10/1968 | Norwood | 128/87 R X |
| 3,640,273 | 2/1972 | Ray | 128/87 R |
| 3,719,187 | 3/1973 | Ulansey | 128/87 R X |
| 3,776,225 | 12/1973 | Lonardo | 128/87 R X |
| 3,975,015 | 8/1976 | Owens et al. | 128/87 R X |
| 4,151,842 | 5/1979 | Miller | 128/87 R |
| 4,190,902 | 3/1980 | Rhee | 128/87 R X |

Primary Examiner—Stephen C. Pellegrino
Attorney, Agent, or Firm—Henri J. A. Charmasson

[57] ABSTRACT

A splint particularly suitable for immobilizing the elbow or wrist articulations of a patient during administration of an intravenous solution. The splint comprises an elongated rigid member which is applied below the articulation and is secured to the patient's limb above and below said articulation by a pair of straps engaged into slots at both ends of the rigid member, then wrapped around the patient's limb and secured by means of material similar to the product sold under the trademark Velcro ® covering the ends of said straps.

2 Claims, 7 Drawing Figures

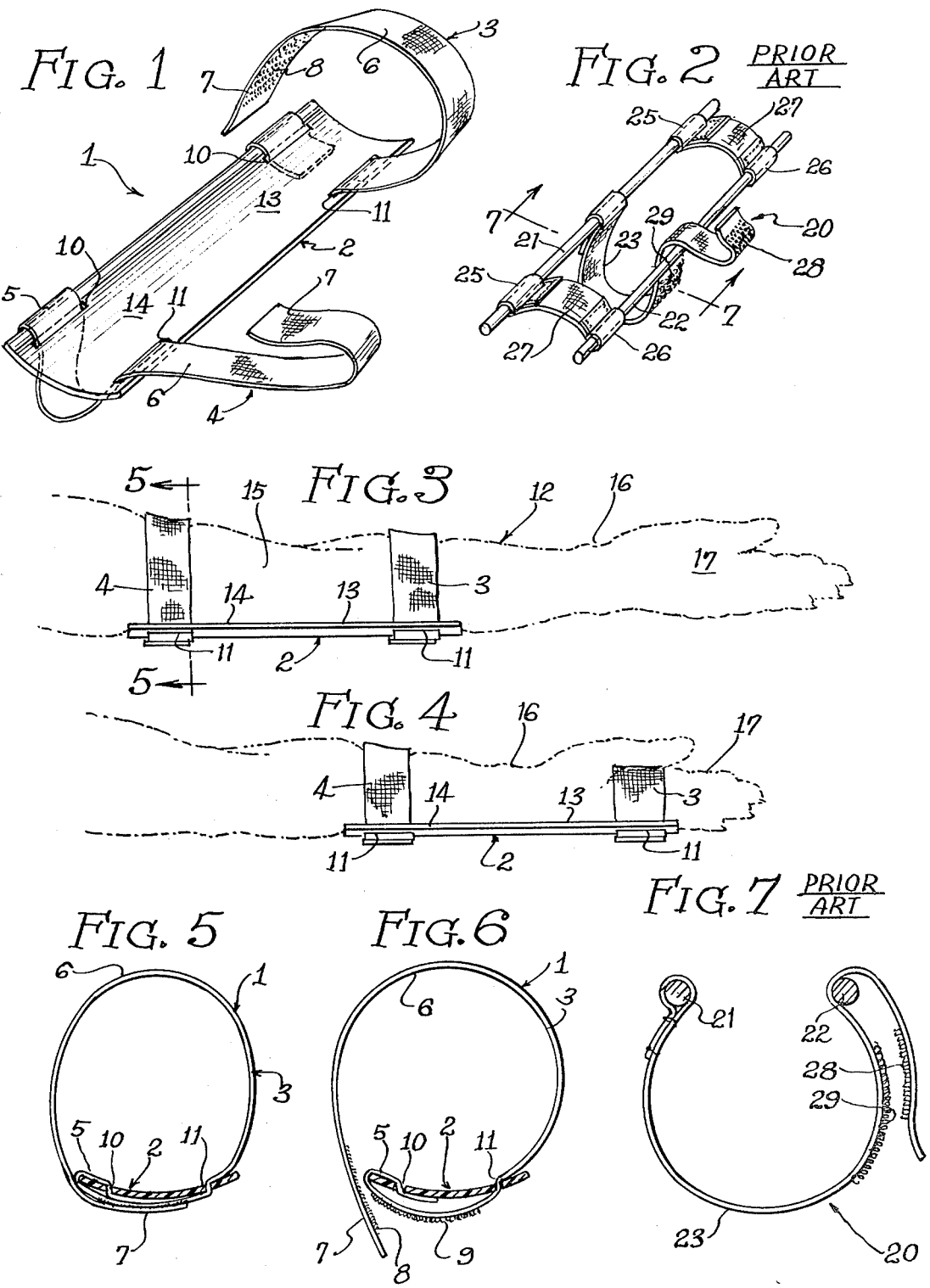

SPLINTING DEVICE

BACKGROUND OF THE INVENTION

Prior art devices have been plagued with limitations, one of which is awkward bracing apparatus which impinge upon the soft tissues of a patient. This factor is extremely critical in view of accident victims whose limbs are often swollen and/or bleeding and who suffer further trauma when abrasive splinting and bracing devices are applied. Applicant's device is directed toward alleviating this problem by providing a splint mechanism which renders structural support directly below a point of articulation rather than primarily above it, as is the case with the prior art. This concept can best be understood with reference to the standard anatomical position in which the human body is viewed in an erect and upright position; the arms are placed so that the elbow joints are fully straightened and the hands rotated so that the palms face forward. The palm side (ventral) is therefore distinguished from the posterior side (dorsal). Prior art devices tradionally employ rigid support members (rods) on the ventral surface, thus incurring a minimal of four pressure points upon the soft tissues of a patient's limb. Applicant's invention, however, utilizes a structural support member on the dorsal side directly below the articulation point (as in the elbow), which provides a fulcrum of bone tissue at one point and the subtle pressure of a pair of resilient straps on the ventral surface. This innovation provides a significant improvement over prior art devices in that minimal tissue damage results, yet the steadying necessary for intravenous application and/or bandaging is achieved.

Another distinction between the prior art is the use of a single longitudinal support member which renders bracing along the length of a limb. This feature is bifurcated in the prior art and is traditionally utilized on the ventral surface of the limb.

Applicant's device represents a further improvement by the incorporation of slots in the rigid support member which allow for easy removal of the engaging straps which pass therethrough in the event of soiling (as frequently occurs in accident and/or trauma contexts), or attrition.

SUMMARY OF THE INVENTION

The invention is a splinting and bracing mechanism designed for immobilizing the limb of a patient during the administration of intravenous solution and/or bandaging. A longitudinal curved rigid support member is provided which fits the contour of a limb and therefore provides comfortable and substantial steadying for purposes of delicate medical procedures. The anatomical orientation of the support member can be designed to accommodate a variety of limb configurations. In the case of the elbow and wrist articulations, the same splint has been found to be equally effective, i.e., the bone pressure point of the olecranon process (of the elbow articulation) and carpal arrangement of the hand bones provides a convenient and efficient fulcrum for steadying means.

Securing means is provided above and below the articulation point by a pair of straps engaged into slots and secured at both ends. The straps are secured by means of mating Velcro-type material covering the ends of said straps. The straps are engaged into slots of the longitudinal curved support member for easy removal in the event of soiling and/or attrition, thereby obviating the necessity of replacing the entire unit.

An object of the present invention is the provision of an improved bracing mechanism for intravenous and other delicate medical administrations. Another object is the provision of a longitudinal support member which is contoured to a limb to be steadied. Another object is the provision of a slotted elongated support member which allows for easy replacement of the straps which pass therethrough in the event of replacement needs. Yet another object is the provision of a bracing mechanism which is comfortable to the patient and which incurs a minimal amount of discomfort and stress upon the delicate tissues of a limb. Yet another object of the invention is the provision of an improved bracing mechanism which is adaptable to a variety of splinting situations.

Other objects and many of the attendant advantages of the instant invention will be better understood by reference to the following description of the drawing.

BRIEF DESCRIPTION OF THE DRAWING

FIG. 1 is a perspective view of the instant invention;

FIG. 2 is a perspective view of a typical prior art device;

FIG. 3 is a side elevational view of the instant invention illustrating the elbow articulation support means;

FIG. 4 is a side elevational view of the instant invention showing the wristbone articulation support means;

FIG. 5 is a sectional view taken along line 5—5 of FIG. 3;

FIG. 6 is a sectional view which illustrates the relationship between two mating straps of Velcro-type material; and FIG. 7 is a cross sectional view taken along line 7—7 of FIG. 2.

DETAILED DESCRIPTION OF THE PREFERRED EMBODIMENT

The overall configuration of the splinting device is best seen in FIG. 1 wherein a splint is generally shown at 1 in perspective view with end straps 5 engaged through slots 10 and captured therein in the respective splint halves 13, 14. The loop formed by engagement into slots 11 is shown in phantom on the underside of support member 2 of half 14 which emerges therethrough to form straps 6, 4 terminating in end strap 7. Straps 6, 3 of respective half 13 illustrates end strap 7 with hook surface 8 thereon.

FIG. 2 illustrates a typical prior art splint 20 having rod members 21, 22 engaged into securing loops 25, 26. Strap 233 is secured to rod 21 at the central portion thereof. Straps 28, 29 have Velcro-type mating portions of interlocking material for securing the assembly.

FIG. 3 is a side elevation view of the instant invention which illustrates the longitudinal support member 2 along the dorsal surface of an elbow joint 15. Halves 13 and 14 of longitudinal support member 2 engage straps, 3, 4 from dorsal to ventral perspective in proximity to an upper arm 12 in the case of strap 4 and between the elbow joint 15 and hand 17 in the case of strap 3. Strap 3 is designed to secure the elbow articulation and is in closer proximity to that articulation than the strap 4.

FIG. 4 is a side elevation view which illustrates the use of the longitudinal support 2 along the dorsal surface of a wrist 16 between an arm 12 and a hand 17. Halves 13, 14 of rigid longitudinal support member 2 can again be seen to engage straps 3, 4 from a dorsal to ventral orientation.

FIG. 5 illustrates an overall perspective of the securing mechanism in relation to the longitudinal support member 2 in which end strap 5 is shown captured in slot 10, traverses the underside of support member 2, and passes through the slot 11 of straps 3, 6, terminating in end strap 7 which is coated with Velcro-type material, said securing means being best illustrated in FIG. 6 which is a detailed view of the interrelationship between the slotted longitudinal support member 2 having slot 10 containing captured end 5 which traverses the undersurface of the rigid support member and becomes loop 9 coated with Velcro-type material for mating engagement with strap 8.

FIG. 7 exemplifies the securing configuration of the prior art splint 20 of FIG. 2 in which rod 21 is shown captured by strap 23 and strap 29 is shown partially capturing rod 22 and terminates in end strap 28 which is coated with Velcro-type material for interlocking engagement with strap 29.

It should be understood that the instant specification is descriptive of the preferred embodiment only and any modifications within the capability of one ordinarily skilled in the art are similarly included within the spirit and scope of the invention as set forth in the appended claims.

What is claimed is:

1. A splint for immobilizing a limb articulation of a patient which comprises:
   a flat elongated rigid member;
   first means for attaching the member to the patient's limb on one side of said articulation;
   second means for attaching the member to the patient's limb on the opposite of said articulation;
   each one of said first and second means for attaching comprising:
   a separable strap, having on one side a first interlocking means and on the other side a second interlocking means cooperating with the first interlocking means to form a breakable fastener,
   said strap having one end section engaged to the right side of the member through a first opening,
   then running parallely to and underneath said flat elongated member, then passing through a second opening in the opposite side thereof,
   the extremity of said end section being captured between the member and that portion of the strap running underneath the member,
   the strap having no permanent means for securing it to the member.

2. The splint claimed in claim 1 wherein said member is latitudinally curved to follow the contour of said limb.

* * * * *